United States Patent [19]

Caron et al.

[11] Patent Number: 5,810,943
[45] Date of Patent: Sep. 22, 1998

[54] WASHER APPARATUS WITH WASTE WATER PH NEUTRALIZATION SYSTEM AND METHOD FOR THE PH NEUTRALIZATION OF WASTE WATER

[76] Inventors: Daniel Caron, 189 Bourguignon, Beauport, Quebec, Canada; Stephane Lynch, 269 Du Charron, St-Augustin-de-Desmaures, Quebec, Canada; Daniel Giguere, 105 De La Montagne, St-Tite-des-Caps, Quebec, Canada; Richard Boutin, 293 Ader, Beauport, Quebec, Canada

[21] Appl. No.: 758,681

[22] Filed: Nov. 27, 1996

[51] Int. Cl.⁶ ...................................................... B08B 7/04
[52] U.S. Cl. ............................ 134/18; 119/450; 119/458; 119/479; 119/517; 119/527; 134/3; 134/27; 134/28; 134/29; 134/41; 210/96.1; 210/143; 210/743; 210/749; 364/499; 364/500
[58] Field of Search .................................. 210/96.1, 143, 210/743, 749; 119/450, 458, 479, 517, 527; 134/56 R, 3, 18, 27, 28, 29, 41; 364/499, 500

[56] References Cited

U.S. PATENT DOCUMENTS

| | | | |
|---|---|---|---|
| 3,899,294 | 8/1975 | Magiros | 210/743 |
| 4,239,493 | 12/1980 | Niemi et al. | 23/230 A |
| 4,374,681 | 2/1983 | Schuenemen | 148/6.14 R |
| 4,830,757 | 5/1989 | Lynch et al. | 210/743 |
| 5,246,594 | 9/1993 | Stegemann et al. | 210/743 |
| 5,380,485 | 1/1995 | Takahashi et al. | 422/62 |

FOREIGN PATENT DOCUMENTS

| | | |
|---|---|---|
| 197804 | 4/1978 | Germany. |
| 922085 | 4/1982 | U.S.S.R. . |

OTHER PUBLICATIONS

"The Value You Expect", AMSCO Scientific Advertising Brochure, SI–6020, Oct. 1993.

"4000 Series Cage and Rack Washer—AMSCO pH–13 Conductivity Board" 1 pg., 1996.

*Primary Examiner*—Stanley S. Silverman
*Assistant Examiner*—Betsey J. Morrison
*Attorney, Agent, or Firm*—Fay, Sharpe, Beall, Fagan, Minnich & McKee

[57] ABSTRACT

A washer apparatus (10) includes a washing chamber (W) with a plurality of spray nozzles (N) and a pump (P1) for circulating the washing fluid (F) through the spray nozzles (N) for cleaning the contents of the washing chamber (W). A pH sensor (20) contacts the washing fluid (F) and a digital pH controller (30) connected to the pH sensor (20) generates digital pH values of the fluid (F). An acid neutralizing system (80) and an alkaline neutralizing system (90) are provided for selectively injecting acid neutralizer and alkaline neutralizer into the reservoir (S, T), respectively. An electronic controller (12) controls the operation of the washer (10) and the acid and alkaline neutralizer injection systems (80, 90) in response to the pH of the washing fluid (F) as determined by the digital pH controller (30).

8 Claims, 13 Drawing Sheets

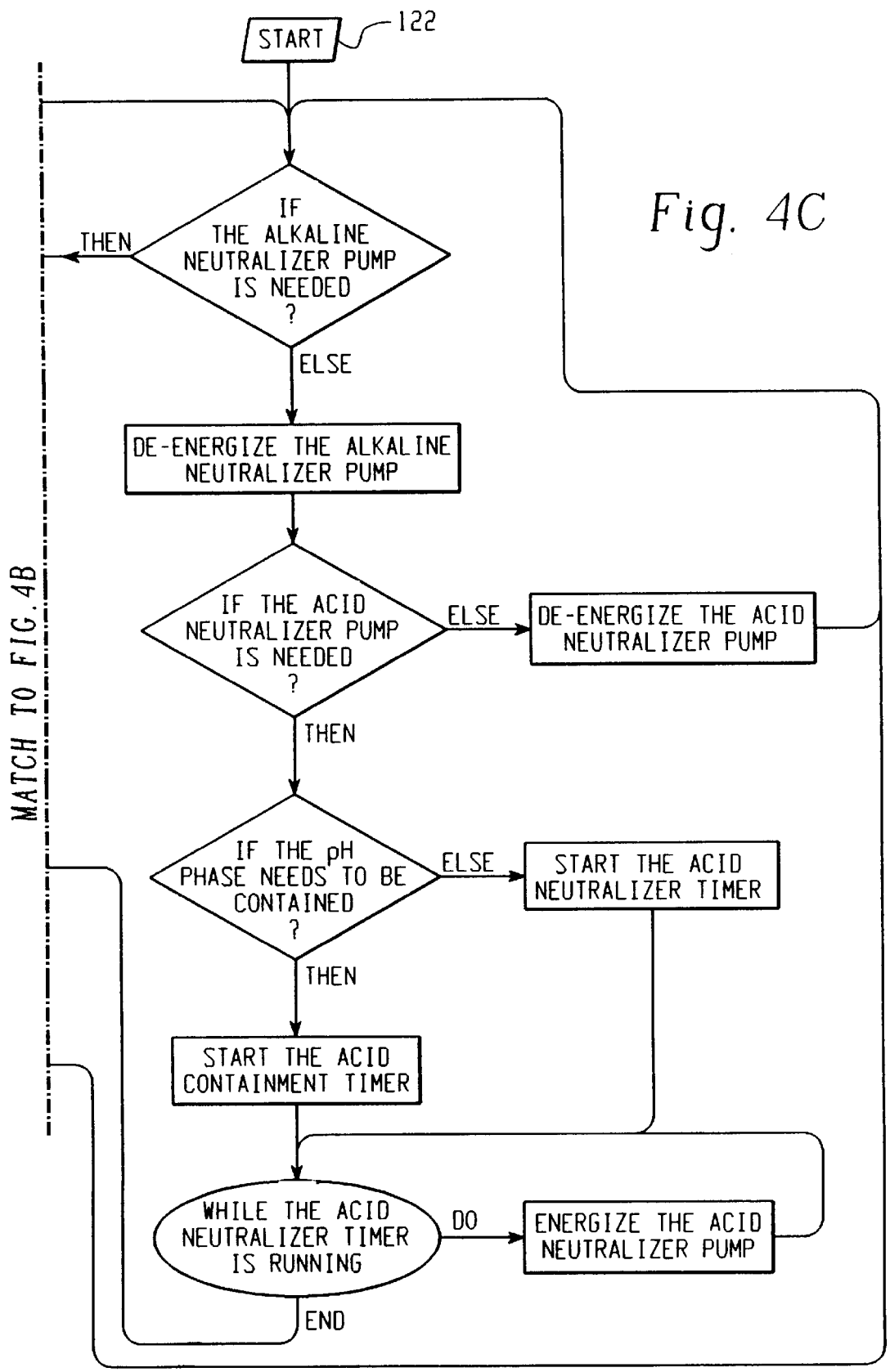

WASHER APPARATUS WITH WASTE WATER PH NEUTRALIZATION SYSTEM AND METHOD FOR THE PH NEUTRALIZATION OF WASTE WATER

BACKGROUND OF THE INVENTION

The present invention relates to the washing and disinfecting arts. It finds particular application in conjunction with a washer apparatus including a waste water pH neutralization system for pH neutralizing the washer waste water prior to its disposal into a sewer system or the like. The present invention also finds particular application in conjunction with a method for pH neutralizing waste water from a washer or similar apparatus in an accurate, easy to control, and "user-friendly" manner.

An increasing concern for the earth's environment has resulted in stringent regulations that require manufacturers, health care providers, testing labs, and others to monitor and control the content and quality of the waste water or effluent resulting from their operations. One area of particular concern for regulators has been the discharge of waste water from these laboratories, health care, and other facilities that has a pH that is significantly less than or greater than neutral.

The dumping of acidic or alkaline effluent into the sewer system can negatively impact the sewage treatment process and can ultimately impact the plants and animals living in or adjacent to streams, rivers, and lakes, or those animals that consume the water. Many plants and animals living in and around streams, rivers, and lakes are sensitive to the pH level of the water and cannot survive if the pH of the water varies significantly from its natural level. Thus, government regulations now often require that any waste water be essentially pH neutral prior to its disposal into the sewer system or directly into the environment. This requires that the pH of the waste water be manipulated from either its acidic condition (low pH of 1–6) or its basic condition (high pH of 8–14) to a value that at least approximates a neutral pH condition of about 7, for example, a pH level of 6.5–7.5.

The animal testing laboratory and health care fields are two disciplines where regulations increasingly require the pH neutralization of the waste water which results from washing operations performed on the laboratory equipment and medical devices and equipment. There has thus been found a need to provide a washing system for use in these and other environments which includes a waste water pH neutralization system that is easy to operate, adjustable, and accurate.

One prior system relies upon the injection of a fixed dose of neutralizer into the waste water without regard to the actual pH of the waste water. This prior system does not accurately neutralize the waste water and could even result in increasing or decreasing the pH out of the near neutral range.

Another prior system is an analog system that does not allow the operator to accurately read the pH of the waste water. The pH sensor is immersed in known, calibration solutions to generate analog output signals. Potentiometers are adjusted to mark the high and low pH setpoints. Thereafter, the setpoints are only adjustable by recalibration. The analog system is merely a one-way system that does not allow the operator of the apparatus to program the system with high and low pH setpoints to establish an acceptable or target pH range for the ultimate pH of the waste water. It does not even tell the operator the measured pH.

The present invention is therefore directed to a method and apparatus which overcomes these problems and others.

SUMMARY OF THE INVENTION

In accordance with one aspect of the present invention, a washer apparatus is provided. A washing chamber has a plurality of spray nozzles and a pump circulates the washing fluid through the washing nozzles for cleaning the contents of the washing chamber. A digital pH controller is connected to a pH sensor in contact with the washing fluid for sensing the pH of the washing fluid. The digital pH controller is adjustably programmed with a high pH setpoint and a low pH setpoint. An acid neutralizer injection system and an alkaline neutralizer injection system selectively inject acid neutralizer and alkaline neutralizer into the washing fluid. An electronic controller is connected to the digital pH controller and receives digital pH values from the pH controller. The electronic controller also transmits the high and low pH setpoints to the digital pH controller and selectively operates the acid and alkaline neutralizer injection systems in response to the digital pH values received from the pH controller. In this manner the acid neutralizer and alkaline neutralizer are injected into the reservoir as needed to alter the pH of the washing fluid in the reservoir.

In accordance with another aspect of the present invention, a method for pH neutralizing washing fluid is provided. The washing fluid is collected and the pH of the washing fluid is sensed. A digital pH value of the collected fluid is generated and compared to high and low digital pH setpoints. In accordance with the digital comparison of the digital pH value and the high and low digital pH setpoints, either an acid neutralizer or a base neutralizer is added to the collected washing fluid until the sensed pH of the collected washing fluid is between the high and low pH setpoints.

The present invention has numerous advantages over the prior art and provides an automatic and easily controllable system for effectively controlling the pH of washer waste water so that it is within an acceptable range.

Another advantage of the present invention is that an operator of the washer apparatus can enter the high and low pH setpoints, between which the final pH of the washing water is to fall before its evacuation from the washer reservoir.

Another advantage of the present invention is that it maintains a hard copy record of the final pH of the waste water and other process parameters as desired.

Another advantage of the present invention is that it allows the final pH of the waste water to be accurately controlled and monitored.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 4 including FIGS. 4A–4C, is a flow chart illustrating modulation of the neutralizer pumps;

FIG. 5 including

DETAILED DESCRIPTION OF THE PREFERRED EMBODIMENTS

Figure 1:
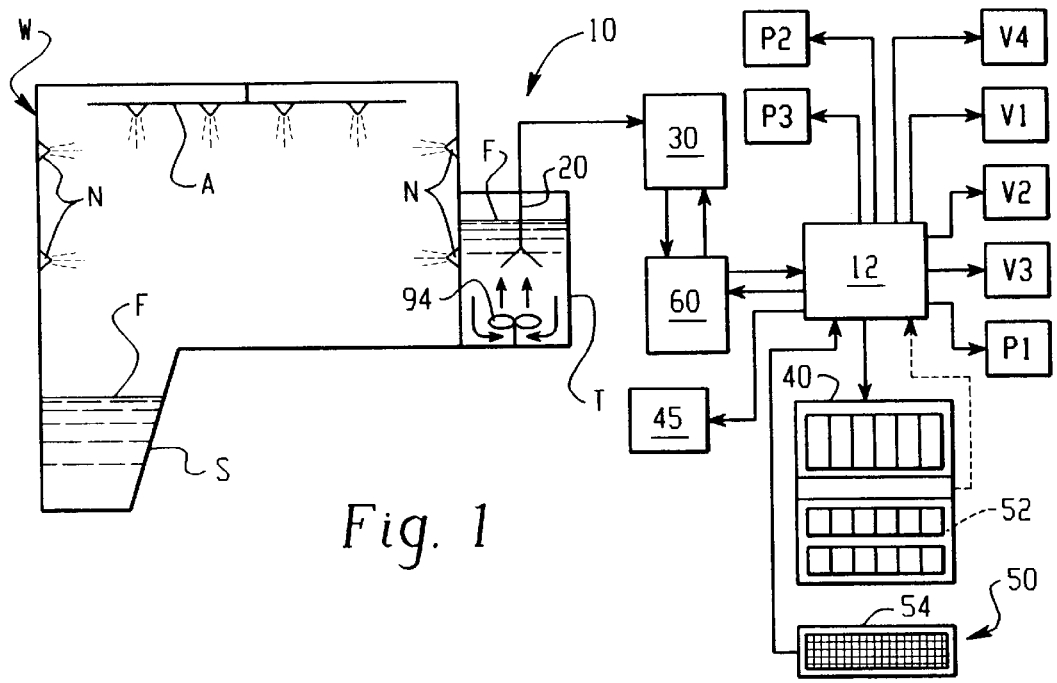
FIG. 1 is a schematic view of the fluid flow system of a washer apparatus in accordance with the present invention.
Figure 2:
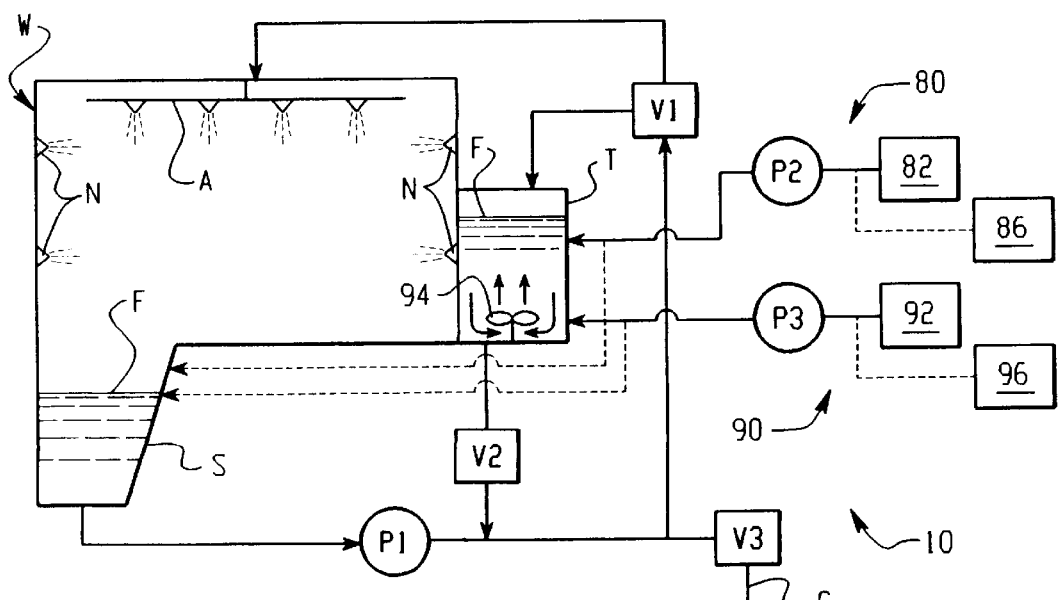
FIG. 2 is a schematic view illustrating the electronic control system of the washer shown in FIG. 1.
Figure 3A:
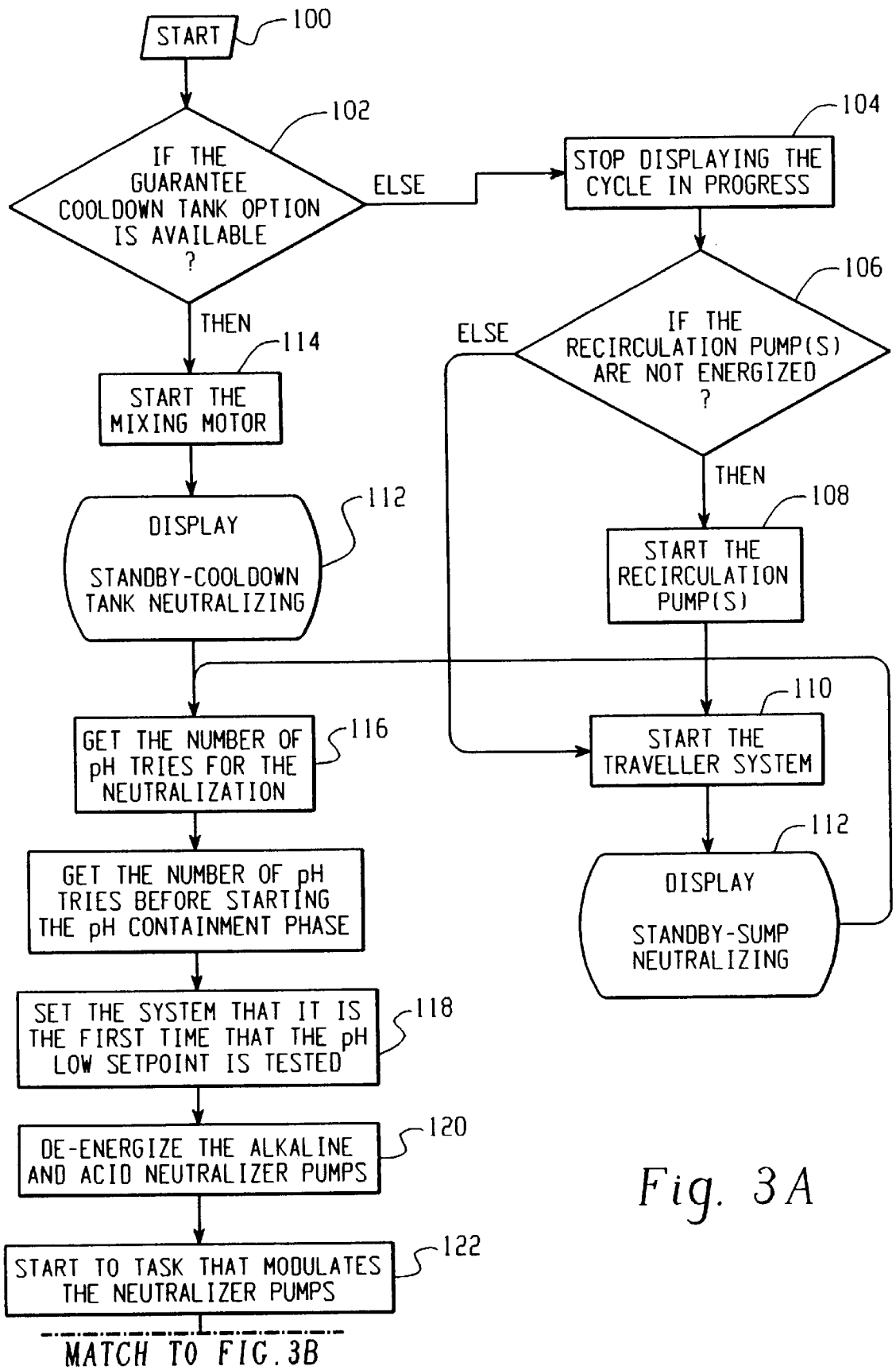
FIGS. 3A–3E taken together are a flow chart illustrating pH neutralization in accordance with the present invention.
Figure 3B:
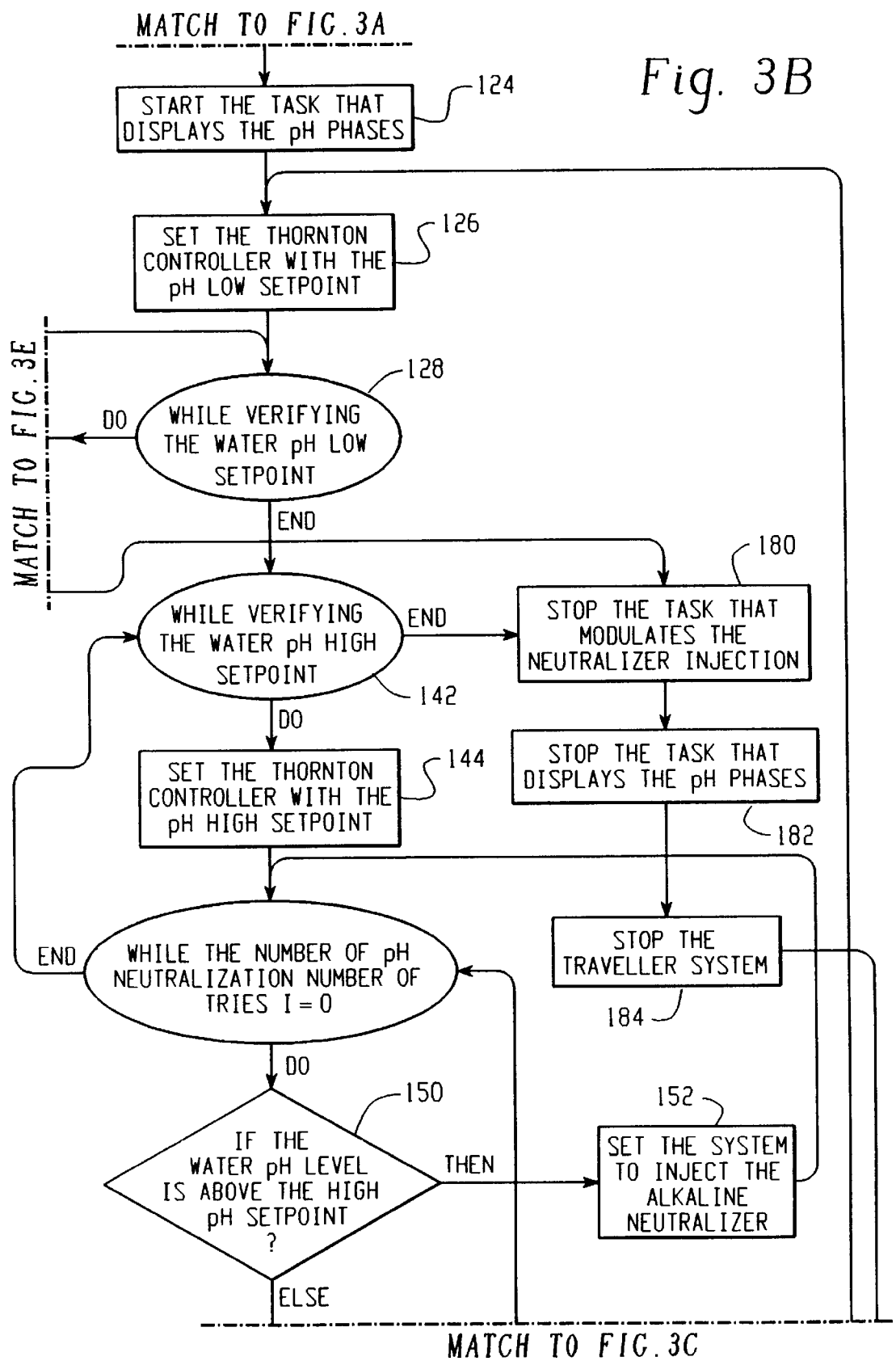
Figure 3C:
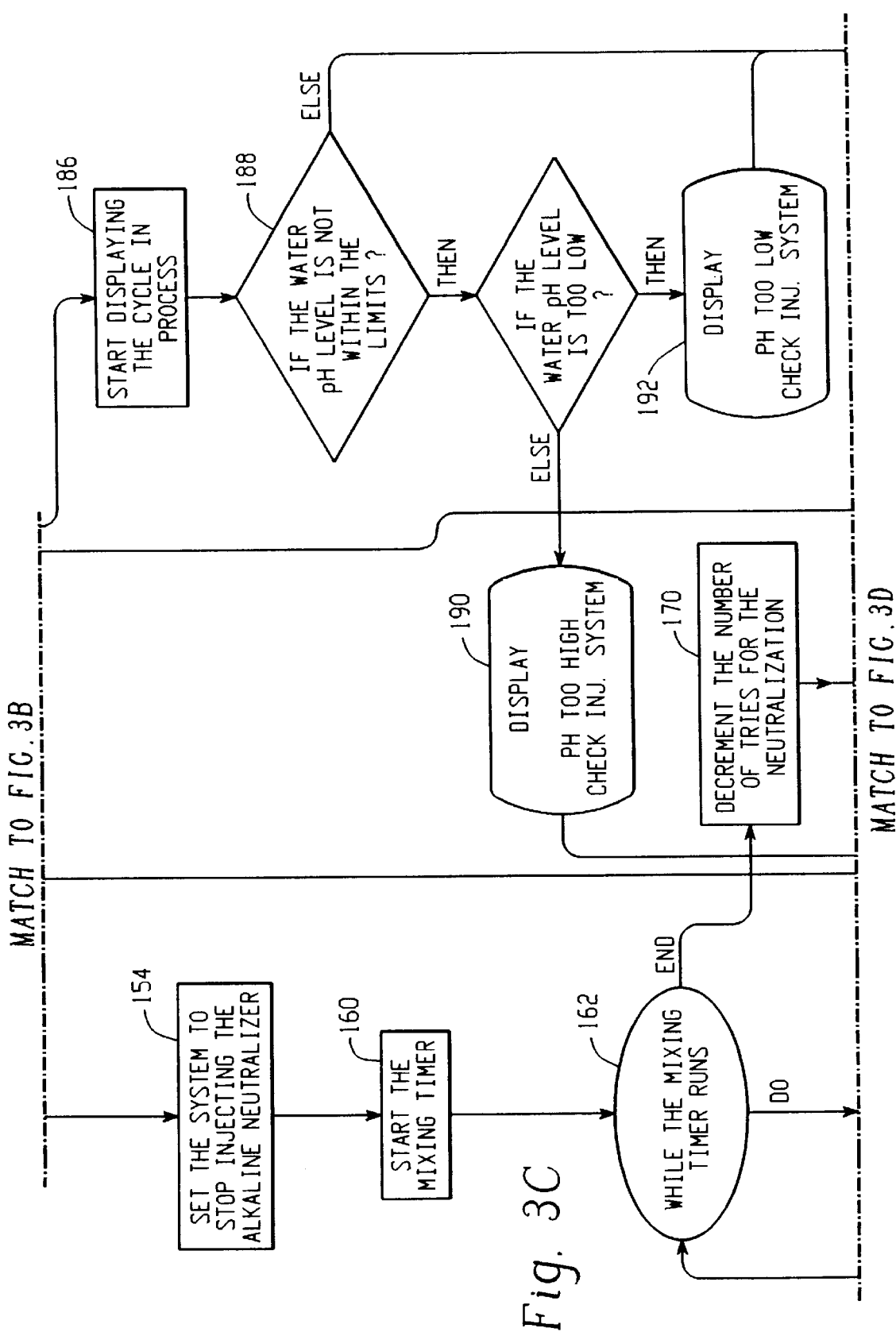
Figure 3D:
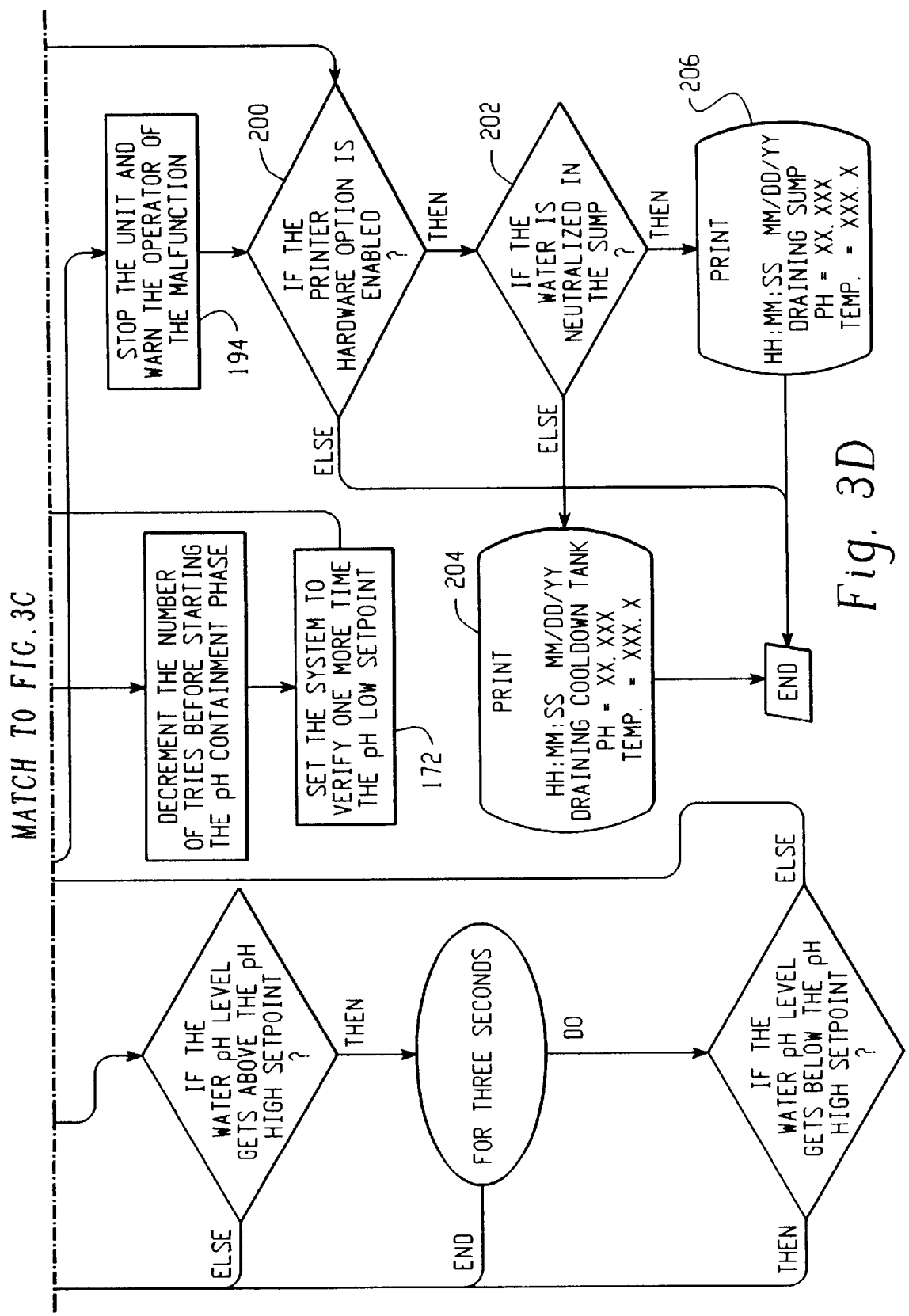
Figure 3E:
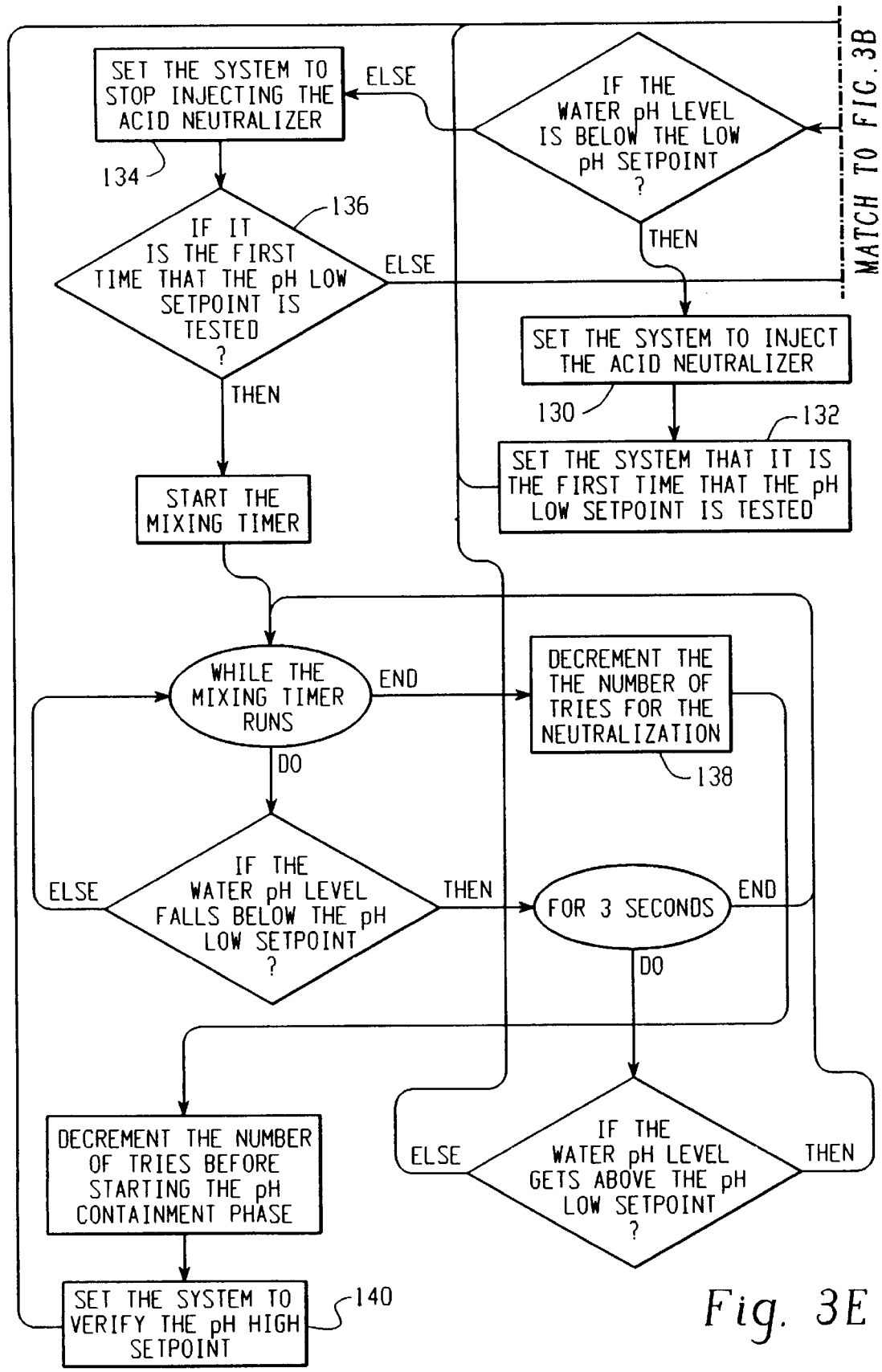

Referring now to the FIGURES as described above, with particular reference to FIGS. 1 and 2, a washer apparatus 10 has a washing chamber W into which medical devices, containers, laboratory animal cages, and other items are placed for washing and sanitation. A sump S collects a washing fluid F which is usually water mixed with one or more detergents, cleaning solutions, corrosion inhibitors, disinfectants, and other chemicals to facilitate the cleaning and rinsing of the contents placed within the chamber W. A recirculation pump P1 (FIG. 2) is in fluid communication with the sump S and, during washing operations, pumps the washing fluid F from the sump S through a valve V1 to a washing arm A and washing nozzles N within the washing chamber W of the apparatus 10.

The washer 10 as shown herein includes an optional cooldown tank T to which the washing fluid F is pumped by the pump P1 through the valve V4. The cooldown tank T is provided, when desired, to cool the temperature of the washing waste water fluid F prior to its pH neutralization and prior to the discharge of the fluid F into a sewer system or directly into the environment. However, those skilled in the art will certainly recognize that the present invention 10 can be configured without a cooldown tank T and that the pH neutralization operations may be carried out in the sump S or in any other reservoir or fluid storage location provided in conjunction with washer 10. The recirculation pump P1 is in selective fluid communication with an outlet line or drain conduit C through a valve V3 for evacuating the waste washing fluid F from the sump S of the washer 10 into a sewer system, a holding tank or holding pond, or directly into the environment subsequent to the pH neutralization of the fluid F as described herein. If the pH neutralization is carried out in cooldown tank T, the valve V2 is opened to drain the fluid F from the tank T under the force of gravity. The pump P1, the valves V1, V2, V3, and V4, and other components and washing functions of the washer apparatus 10 are controlled by an electronic washer controller 12 (FIG. 1) as is discussed in detail below, which may be, for example, an Allen-Bradley, Siemens, or other commercially available controller.

A pH sensor or probe 20 is immersed in or otherwise caused to be in contact with the waste wash water F in the tank T or sump S. The pH probe 20 is electrically connected to an electronic digital pH controller 30, such as a Thornton controller. The controller 30 receives voltage signals from the pH probe 20 and converts the voltage signals into digital pH values representative of the pH level of the fluid F. The electronic washer controller 12 and the pH controller 30 are electrically connected to a gateway or local-area-network (LAN) 60 as is described below, for two-way digital communication between the pH controller 30 and the electronic washer controller 12. Electronic controller 12 is electrically connected to and controls a visual display, preferably an LCD alpha-numeric display 40 for displaying the sensed pH value of the fluid F. A printer 45 is preferably provided and connected to electronic controller 12 to print a hard copy of any of the information displayed on the display 40. This printed information may be required for regulatory compliance records or for internal audit records.

An input system 50, preferably a keypad or keyboard 54, enters new high and low pH setpoints. Optionally, the input system includes a touch sensitive screen 52 (which is preferably part of the display screen 40) for selecting cycles, starting operations, and the like. Input system 50, including keyboard 54 and optional touch screen 52, are preferably electrically connected to electronic controller 12 for inputting data into controller 12. The electronic pH controller 30 is preferably electrically connected to the output display 40, the printer 45, the input system 50, and other components of washer 10 through a gateway or local-area-network (LAN) system 60 and through electronic washer controller 12 using known electrical connections such as one or more RS-232 communications ports or the like. The connection of pH controller 30 with LAN 60 allows for the easy connection of numerous other components to the LAN, and thus to the controller 30, as desired for two-way communication. This enables input setpoints and other information to be communicated to the screen 40 for display. The washer controller 12, as described above, is also connected to the gateway 60 to provide two-way communication between the washer controller 12 and other devices connected to the LAN. The washer controller 12 receives digital pH values from the pH controller and controls the pH neutralization process accordingly. Those skilled in the art will recognize that, although shown as separate components herein for clarity, the pH controller 30 and the washer controller 12 can be formed integrally with one another and be provided by the same electronic circuit.

The operation of the pH neutralization system of the washer apparatus 10 can be best understood with reference once again to FIG. 2 wherein the fluid flow system of the washer apparatus 10, including the pH neutralization system, is shown. An acid neutralizer injection system 80 includes a supply tank of acid neutralizer 82 in selective fluid communication with the washer 10, and specifically the cooldown tank T, through an acid neutralizer pump P2. Similarly, an alkaline neutralizer injection system 90 includes a supply tank of alkaline neutralizer 92 in selective fluid communication with the tank T of the washer apparatus 10 through an alkaline neutralizer pump P3. The acid neutralizer in supply tank 82 and the alkaline neutralizer in supply tank 92 may be any suitable alkaline and acid solutions, respectively. Also, a supply tank of alkaline detergent 86 or a supply tank of acid detergent 96 can be provided, and the alkaline detergent and acid detergent contained therein can be used to neutralize acid and alkaline washing fluid F, respectively. The pumps P2, P3 are connected to the washer controller 12 such that either of the pumps P2, P3 can be energized intermittently, as required, for pH neutralization operations. More specifically, if the operation of the pH probe 20 and the pH controller 30 indicates that the pH of the fluid F is acidic, the controller 12 causes the acid neutralizer pump P2 to be energized to dispense a metered amount of acid neutralizer from the supply tank 82 or tank 86 into the fluid F. This operation is repeated until the fluid F in the tank T is no longer too acidic—i.e., no longer has a pH value below the low pH setpoint. Likewise, if the operation of the pH probe 20 and the pH controller 30 indicates that the pH of the fluid F is alkaline, the controller 12 causes the alkaline neutralizer pump P3 to be energized to dispense a metered amount of alkaline neutralizer from the supply tank 92 or supply tank 96 into the fluid F. This operation is repeated until the fluid F in the tank T is no longer too alkaline—i.e., no longer has a pH above the high pH setpoint.

To facilitate the pH neutralization process as described generally above, and to ensure the accuracy of the pH readings at probe 20, the tank T is preferably fitted with a mixing device 94 for circulating the fluid F within the tank T. The recirculation pump P1 and the valve V1 are preferably operated to circulate, and thus mix the fluid F in the sump. Once the fluid F has been pH neutralized such that the pH of the fluid F is between the high and low pH setpoints, the pump P1 is operated and the valve V3 is opened to evacuate the fluid F from the sump S through an evacuation conduit C or the valve V2 is opened to evacuate the fluid F from the tank T through evacuation conduit C under the force of gravity. The display 40 displays to the operator the final pH of the fluid F and other parameters of the pH neutralization process as desired. As mentioned, the operator can then use the printer 45 to obtain a hard copy record of all neutralization operations.

With particular reference to FIGS. 3A–3E, upon the completion of one or more wash or rinse cycles, the operator starts the waste water pH neutralization process at a step 100. A step or means 102 checks to see if a cooldown tank T is present, and if not, steps or means 104 through 112 circulate the fluid F in the sump S. The steps or means 106–108 activate the recirculation pump P1 to mix the fluid F. The step or means 110 starts the traveller system (not shown) of the washer 10. Otherwise, the step or means 114 starts the mixing apparatus 94 in the tank T to mix the fluid F contained within the tank T. In both cases, with or without the cooldown tank T, a step or means 112 visually prompts the operator on display 40 to standby for the neutralizing operations. The process continues with a step or means 116 which determines the number of pH tries for the neutralization and a step or means 118 indicates that this is the first time the low pH setpoint is tested.

Figure 4A:
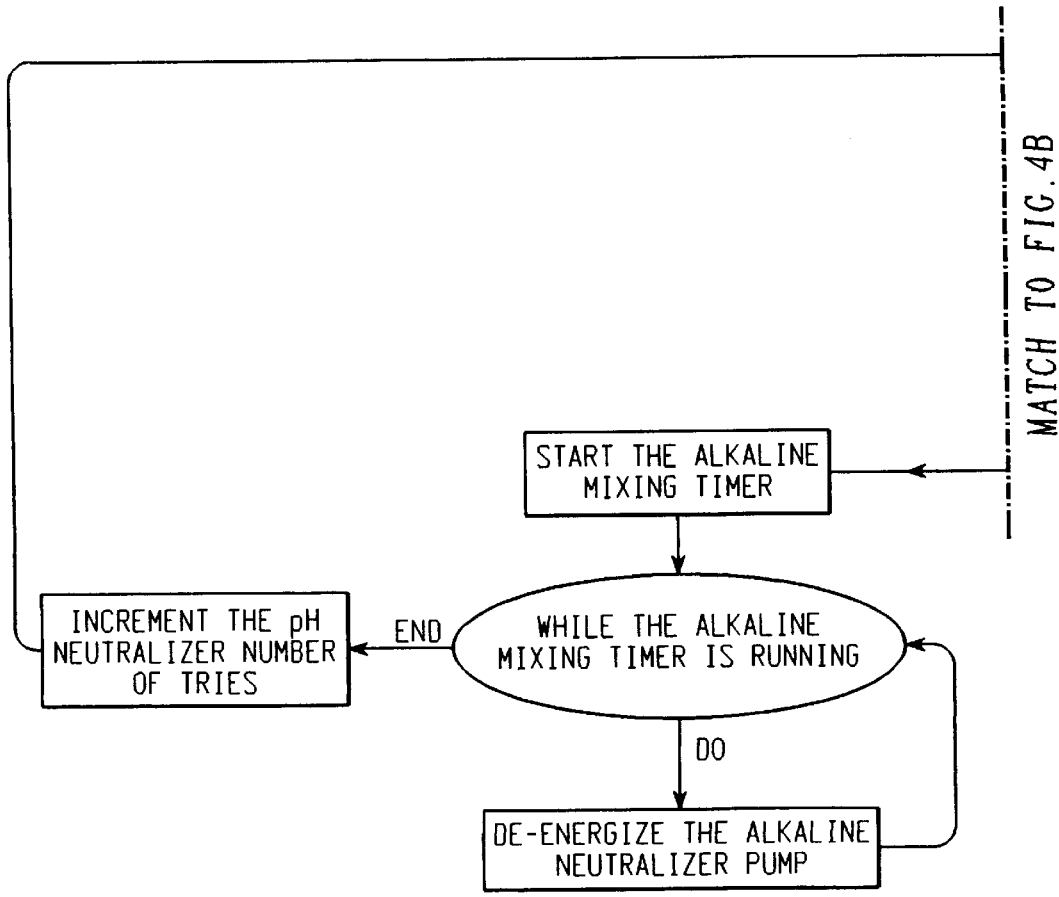
Figure 4B:
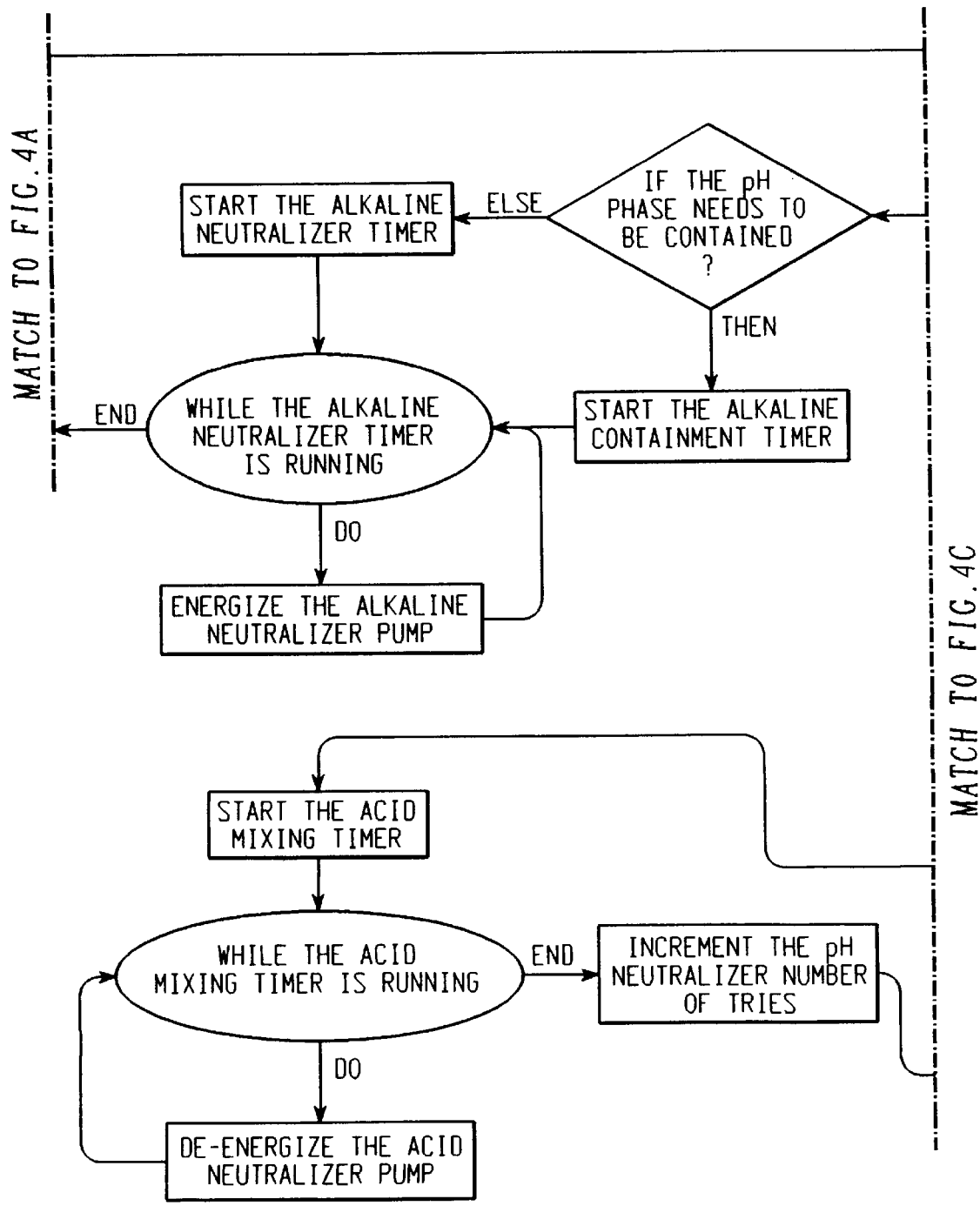

A step or means 120 de-energizes the pumps P2, P3 and a step or means 122 starts the task that modulates or controls the operation of the acid neutralizer and alkaline neutralizer pumps P2, P3. The operations carried out by a step or means 122 are illustrated in full detail in FIG. 4. A step or means 122 selectively energizes the acid and alkaline neutralizer pumps P2, P3, as needed, throughout the neutralization process for predetermined amounts of time to inject a predetermined amount of acid neutralizer and alkaline neutralizer, respectively, into the waste water fluid F contained within the reservoir S,T of the apparatus 10 to cause a neutralization reaction between the neutralizer from supply 82, 92 and the fluid F. The task illustrated in FIG. 4 also controls the timed operation of mixing device 94 as indicated such that, upon the injection of the acid or alkaline neutralizer into the fluid F, the operation of the mixing device 94 ensures that the reaction between the fluid F and the neutralizer from the tank 82, 92 is completed and thus ensures that the fluid F has a consistent pH throughout its volume.

Figure 5A:
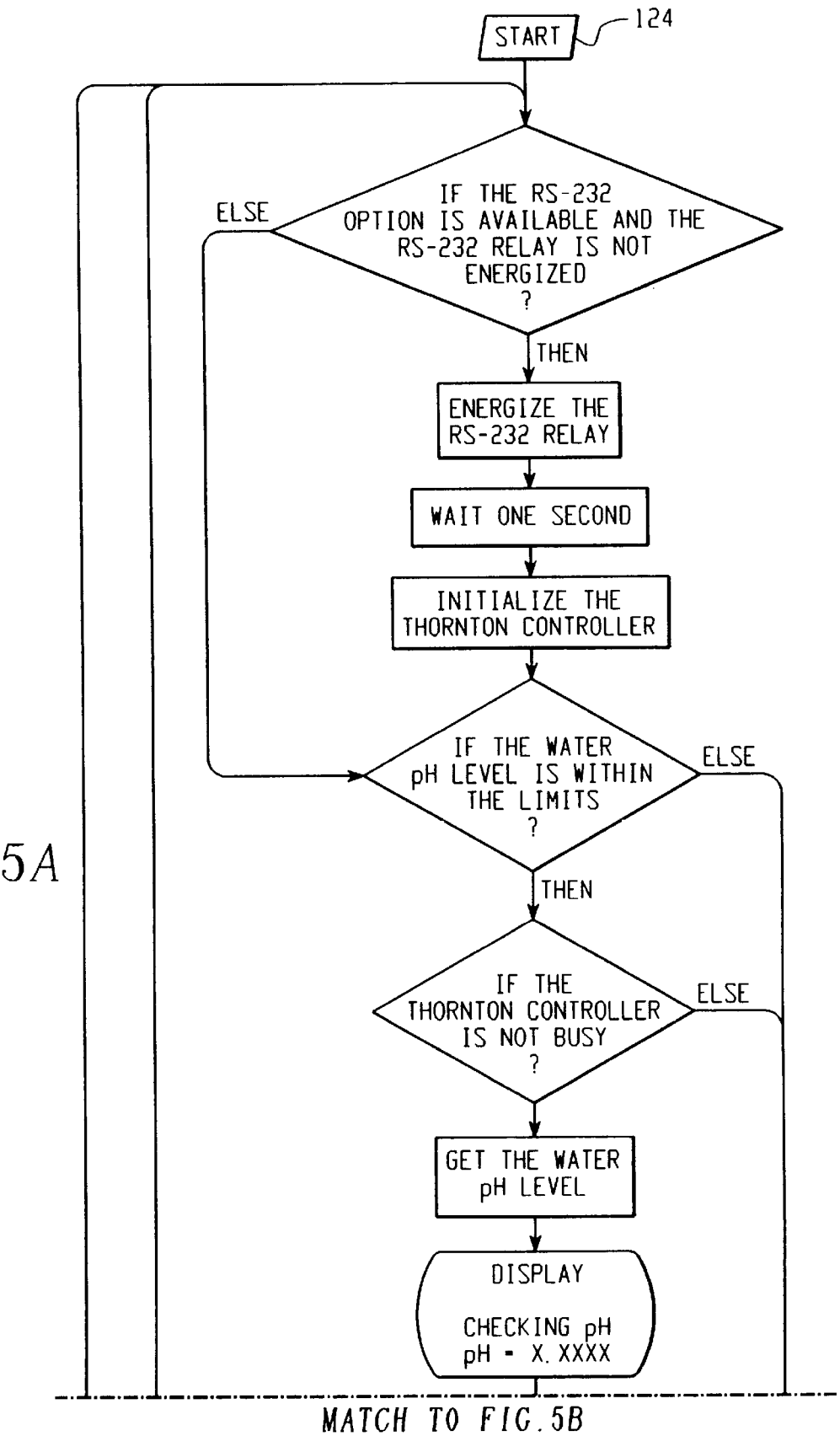
FIGS. 5A and 5B, is a flow chart illustrating display of the pH phases to the machine operator.
Figure 5B:
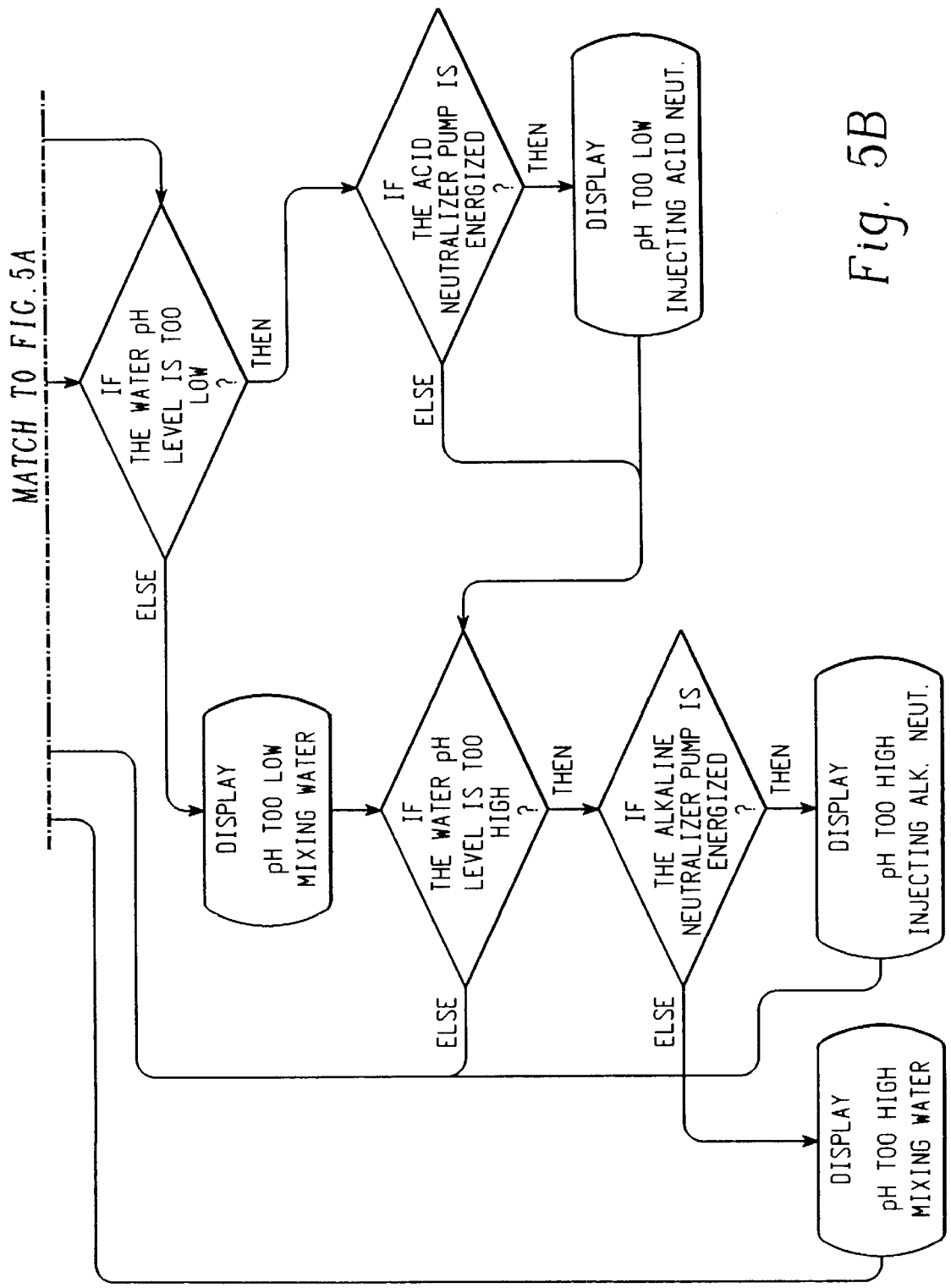

Once the step or means 122 starts the task that modulates the pumps P2, P3, a step or means 124 starts the task that displays the pH phases on the display 40 of the apparatus 10. In general, with reference to FIG. 5, the task that displays the pH phases interrogates the pH controller 30 through an RS-232 connection or the equivalent to receive the current pH of the fluid F so that the current pH is displayed on the display 40. If the sensed pH is out of the acceptable range, the task that displays the pH phases also displays the appropriate message on display 40 to indicate that the pH of the fluid F is either too high or too low and to indicate that the neutralization process is being carried out.

Figure 7:
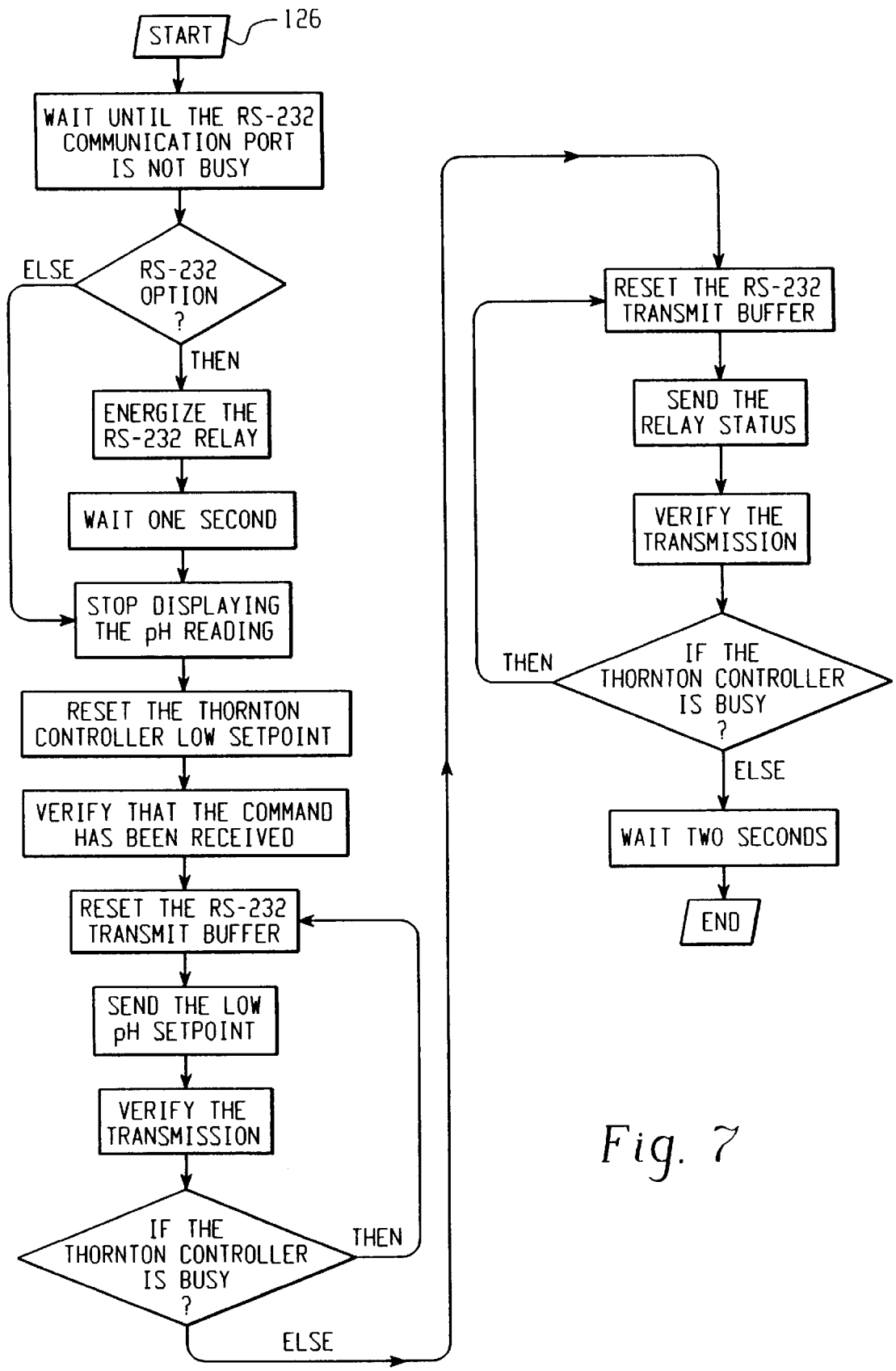

After the starting of the display task at the step or means 124, a step or means 126 sets the low pH setpoint in the pH controller 30. As mentioned above, the low pH setpoint is the lower limit of the acceptable pH range for the fluid F. The operations performed by the step or means 126 are set forth in detail in FIG. 7. The low pH setpoint as entered by a user of the apparatus 10 is communicated to the pH controller 30 through the RS-232 communication connection or the equivalent. After the low pH setpoint is established, the neutralization process moves forward. A step or means 128 checks the current pH of the waste water fluid F in the tank T, the sump S, or other reservoir as applicable. If the pH setpoint is too low (below the low pH setpoint), a step or means 130 causes the acid neutralizer pump P2 to be operated for a selected time to inject a selected, metered dose of acid neutralizer into the fluid F from the supply of acid neutralizer 82. The pump P2 operates under the control of the pump modulating task of FIG. 4. A step or means 132 sets the system to indicate that this is the first time the low pH setpoint has been tested. Once the pH level rises above the low pH setpoint, a step or means 134 stops the injection of the acid neutralizer and checks to see if this is the first time the pH low setpoint has been tested. If this is the first time the low pH setpoint has been tested, then the mixing timer is started by a step or means 136 to operate the mixing device 94 for a selected time to be certain that, upon mixing the fluid F, the pH does not fall below the low setpoint. If the pH does fall below the low pH setpoint upon the mixing, the acid neutralization process is repeated by the step or means 128 to raise the pH of the fluid F above the low setpoint. However, if upon the operation of the mixing device 94 at step 134 the pH level of the fluid F stays above the low setpoint, then the process moves forward to determine if the pH of the fluid F is above or below the high pH setpoint, which is the upper limit of the acceptable pH range for the fluid F.

Figure 6:
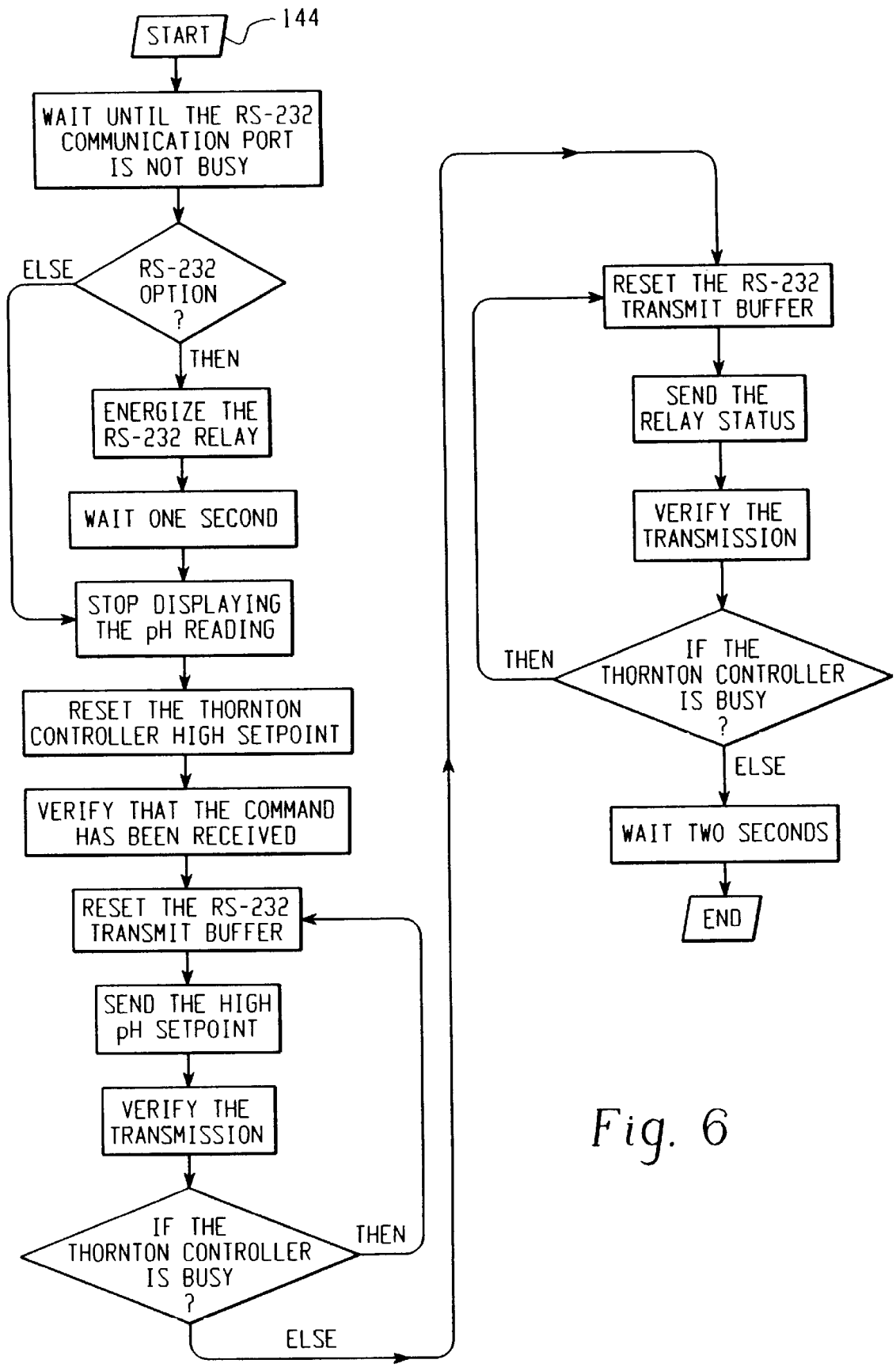
FIG. 6 is a flow chart illustrating setting of the high pH setpoint; and, FIG. 7 is a flow chart illustrating setting the low pH setpoint.

A step or means 138 decrements a counter of the number of neutralization tries and the step or means 140 starts the pH high setpoint verification process beginning with a step or means 142. A step or means 144 sets the high pH setpoint in the pH controller 30 in response to the desired high pH setpoint as entered by the operator of the apparatus 10 using the input system 50. With reference to FIG. 6, the process for setting the high pH setpoint in the pH controller 30 by a step or means 144 is carried out in the same manner as the setting of the low pH setpoint by the step or means 126. Once the high pH setpoint is set and while a neutralization number of tries variable is not equal to zero, the pH of the fluid F is checked by a step or means 150 to determine if the pH is above or below the high setpoint. If the sensed pH is above the high setpoint, a step or means 152 injects a preselected, metered dose of alkaline neutralizer from supply 92 into the fluid F using the pump P3. Once the pH of the fluid F falls below the high pH setpoint, a step or means 154 stops the alkaline neutralizer injection system 90 and commences a fluid mixing operation 160 by the mixing device 94 for a predetermined period of time. If the pH stays below the high setpoint upon being mixed, a step or means 170 decrements a counter of neutralization tries. A step or means 172 verifies that the pH of the fluid F has not moved below the low pH setpoint due to the injection of the alkaline neutralizer solution into the fluid F.

Once the final verification of the low pH setpoint is completed in the same manner as the first verification of the low pH setpoint, a step or means 180 stops the task that modulates the pumps P2, P3 which was started by the step or means 122. A step or means 182 stops the task that displays the pH phases which was started by the step or means 124. A step or means 184 stops the traveller system and other systems of the washer apparatus 10. A step or means 186 starts displaying information regarding the cycle in progress. More specifically, a step or means 188 determines if the final pH of the fluid F is between the high and low setpoints as entered by the machine operator. If the final pH is not within the acceptable range, a step or means 190 or 192 displays an appropriate error message indicating a final pH that is either too high or too low, respectively. A step or means 194 stops the washer cycle and displays an error message to the operator. Otherwise, if the final pH is within the range established by the high and low setpoints, steps or means 188 to 200 check to see if the printer 45 is installed and enabled. If the printer 45 is not available for printing, the fluid F is drained from the tank T or sump S through conduit C as appropriate for the particular configuration of washer 10, and the process is stopped. Otherwise, if the printer 45 is available, the fluid F is drained from the sump S or tank T as appropriate. A step or means 204 or step 206 prints the time, date, final pH value of the fluid, and current status of the system.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for washing animal cages and for the pH neutralization of the spent cage washing fluid, the method comprising:
    (a) positioning at least one soiled animal cage in a washing chamber and cleaning the same with streams of a washing fluid;
    (b) collecting the spent washing fluid used for animal cage washing operations;
    (c) sensing a pH of the collected washing fluid;
    (d) generating a digital pH value of the collected fluid;
    (e) comparing the digital pH value of the spent washing fluid with high and low user-programmed digital pH value setpoints, said high and low setpoints, respectively, corresponding to the highest and lowest acceptable pH values of the spent washing fluid;
    (f) in accordance with the digital comparison of the spent washing fluid digital pH value and the high and low user-programmed setpoints, adding preselected amounts of one of an acid neutralizer and a base neutralizer to the collected washing fluid and mixing the collected washing fluid until one of the set points is crossed;
    (g) repeating steps (c) through (f) until the sensed pH value is between the high and low setpoints.

2. The method as set forth in claim 1 wherein the acid neutralizer fluid is an alkaline detergent and wherein the alkaline neutralizer fluid is an acid detergent.

3. A method of neutralizing residual washing fluid in a laboratory animal equipment washing apparatus, said method comprising:
    (a) collecting the residual washing fluid;
    (b) measuring and displaying at least the digital pH of the collected washing fluid;
    (c) comparing the measured digital pH of the collected washing fluid with user-variable and user-programmed high and low digital pH setpoints, said high and low digital pH setpoints defining a range of acceptable final pH values for said collected washing fluid;
    (d) for a select number of neutralization attempts, adding metered doses of at least one of an acid neutralizer and a base neutralizer to said collected washing fluid to move the sensed digital pH of the collected washing fluid toward the acceptable range of final pH values for the collected washing fluid;
    (e) discharging the collected washing fluid when the final sensed digital pH of the collected washing fluid is within the acceptable range defined by the high and low user-programmed pH setpoints; and,
    (f) displaying an error message to an operator of the animal equipment washing apparatus if the final pH value of the collected washing fluid is not within the acceptable range defined by the high and low user-programmed pH setpoints.

4. The method as set forth in claim 3 further including:
cooling the collected washing fluid prior to sensing the pH of the collected washing fluid.

5. The method as set forth in claim 3 further including:
displaying at least the digital pH of the collected washing fluid and the selected high and low pH setpoints.

6. The method as set forth in claim 5 further including:
printing a hard copy output of at least the final pH of the collected washing fluid, the user-programmed high pH setpoint, and the user-programmed low pH setpoint.

7. A laboratory equipment washing method comprising:
    (a) placing soiled laboratory equipment in a washing chamber and contacting the equipment with a stream of a recirculating washing fluid, said recirculating washing fluid being one of an acidic washing fluid and an alkaline washing fluid;
    (b) after the select washing duration, collecting the recirculating washing fluid;
    (c) sensing a pH of the collected washing fluid and generating a digital pH value corresponding to the sensed pH of the collected washing fluid;
    (d) inputting a digital low pH setpoint as a lowest acceptable digital pH value for the collected washing fluid and a digital high pH setpoint as a highest acceptable digital pH value for the collected washing fluid;
    (e) displaying in a digital format the digital pH value of the collected washing fluid, the digital pH low setpoint, and the digital pH high setpoint;
    (f) for a select number of neutralization attempts:
        (f1) comparing the digital pH value of the collected washing fluid with the low pH setpoint and adding metered doses of an acid neutralizer to the collected washing fluid until the digital pH of the collected washing fluid satisfies the low pH setpoint;
        (f2) comparing the digital pH value of the collected washing fluid with the high pH setpoint and adding metered doses of an alkaline neutralizer to the collected washing fluid until the digital pH of the collected washing fluid satisfies the high pH setpoint;
        (f3) comparing the digital pH value of the collected washing fluid with the low pH setpoint to verify that the sensed digital pH of the collected washing fluid is between the high and low pH setpoints;
    (g) discharging the collected washing fluid only if the sensed digital pH value of the collected washing fluid is between the high and low digital pH setpoints; and,
    (h) displaying an error message if the sensed digital pH value of the collected washing fluid is not between the high and low digital pH setpoints after said select number of neutralization attempts.

8. A method for washing laboratory animal care equipment, said method comprising:

(a) programming a pH neutralization control system with user-programmed digital high and low pH setpoints to establish the highest and lowest acceptable pH values of an effluent washing fluid, respectively;

(b) positioning soiled laboratory animal care equipment in a washing chamber and exposing the equipment to streams of washing fluid;

(c) collecting the washing fluid, sensing the pH of the collected washing fluid, and generating a digital pH value indicative to the sensed pH;

(d) comparing the digital pH value of the collected washing fluid with the user-programmed low pH setpoint and injecting a metered dose of acid neutralizer into the collected washing fluid until the sensed pH is above said user-programmed low setpoint;

(e) comparing the digital pH value of the collected washing fluid with the user-programmed high pH setpoint and injecting a metered dose of base neutralizer into the collected washing fluid until the sensed pH of the collected washing fluid is below said user programmed high setpoint;

(f) repeating steps (d) and (e) until the digital pH value of the collected washing fluid is between the user-programmed high and low pH setpoints, (g) discharging the collected washing fluid as effluent only if the sensed digital pH of the collected washing fluid satisfies both the user-programmed digital high and low pH setpoints;

(h) displaying an error message if the sensed digital pH of the collected washing fluid does not satisfy both the user-programmed digital high and low pH setpoints; and, (i) printing a hard copy output of at least the final digital pH value of the collected washing fluid, the user-programmed digital high pH setpoint, and the user-programmed digital low pH setpoint.

* * * * *